United States Patent [19]
Schmidt et al.

[11] 3,991,316
[45] Nov. 9, 1976

[54] APPARATUS FOR X-RAY EXAMINATION

[75] Inventors: Arthur Schmidt; Wolfgang Henkel, both of Erlangen; Johann Finkenzeller, Tennenlohe, all of Germany

[73] Assignee: Siemens Aktiengesellschaft, Munich, Germany

[22] Filed: Nov. 2, 1973

[21] Appl. No.: 412,528

Related U.S. Application Data

[63] Continuation of Ser. No. 237,710, March 24, 1972, abandoned.

[52] U.S. Cl. .......................... 250/439 R; 250/445 R
[51] Int. Cl.² ......................................... G03B 41/16
[58] Field of Search ........... 250/320, 322, 439, 444, 250/445

[56] References Cited
UNITED STATES PATENTS

| | | | |
|---|---|---|---|
| 1,978,745 | 10/1934 | Franke | 250/322 |
| 3,365,575 | 1/1968 | Strax | 250/445 |
| 3,578,971 | 5/1971 | Lasky | 250/320 |
| 3,609,355 | 9/1971 | Schwarzer | 250/320 |

FOREIGN PATENTS OR APPLICATIONS

| | | | |
|---|---|---|---|
| 938,410 | 10/1963 | United Kingdom | 250/439 |
| 238,079 | 2/1969 | U.S.S.R. | 250/439 |

*Primary Examiner*—Craig E. Church
*Attorney, Agent, or Firm*—Richards & Geier

[57] ABSTRACT

An apparatus for X-ray examination is used for so-called mammagraphic work. It includes an X-ray tube, a supporting surface for the exposure material and a compressing device. The invention is particularly characterized in that a constant distance is maintained between the X-ray tube and the supporting surface for the exposure material and in that the compressing device is adjustable independently from the X-ray tube and/or the supporting surface. By way of example, the compressing device may be a compression tube supported so as to be movable in the direction toward the supporting surface.

3 Claims, 3 Drawing Figures

APPARATUS FOR X-RAY EXAMINATION

This application is a continuation of a co-pending patent application filed Mar. 24, 1972, Ser. No. 237,710, now abandoned.

This invention relates to an apparatus for X-ray examination.

An X-ray examining device for so-called mammagraphic work is known, wherein the supporting surface for the exposure material is adjustable in the direction toward the X-ray tube for compression of the object being examined which lies upon the exposure material. A drawback of this X-ray examining consists in that the film-focus distance, i.e. the distance between the film and the focal point of the X-ray tube, is dependent upon the size of the object being examined. The result is that in each examination the illuminated surface of the film is of a different size. When X-ray pictures produced by such an X-ray examining apparatus are examined in a film examining device, there is a glare of unilluminated bridge edge portions. Furthermore the different geometrical relationships resulting from the variable film-focus distance make difficult a comparison between different patients.

An object of the present invention is to eliminate these drawbacks.

Other objects of the present invention will become apparent in the course of the following specification.

In the accomplishment of the objectives of the present invention it was found possible to eliminate the undesirable variable film-focus distance in an X-ray examining apparatus of the described type and having an X-ray tube, a supporting surface for the exposure material and a compressing device, by maintaining constant the distance between the X-ray tube and the supporting surface for the exposure material and by making the compression device, which can be, for example, a compression tube movable toward the supporting surface, so that it can be adjusted independently from the X-ray tube and/or the supporting surface. This arrangement provides a film-focus distance which always remains the same independently from the size of the object being examined and the extent of the compression. A comparison of the X-ray pictures of different patients is facilitated by the geometrical image proportions which are then always the same.

According to a particularly advantageous embodiment of the present invention the X-ray tube may be provided with a diaphragm having a constant opening for a complete illumination of the exposure material. In this manner due to an illumination of the exposure material which is always complete, the disturbing bright edges upon the X-ray films are avoided. At the same time the servicing of the X-ray examining apparatus is simplified by the elimination of field blinding. Finally this development of the present invention saves the use of heavy tubes which are not transparent to X-rays and which extend up to the object being examined as well as expensive adjustable primary ray diaphragms.

A particularly convenient operation of the X-ray examining device is attained when a compression tube which does not limit the X-rays is made of a transparent material. Such a compression tube permits to control the location of the object being examined even after the compression has taken place. Furthermore, such a compression tube which is light and easy to handle due to the material used can be easily adjusted or exchanged for a differently shaped special tube.

According to a further development of the present invention due to the provision of a ray cone which always illuminates the entire exposure material, an ionization chamber can be provided in the ray direction behind the supporting surface for the exposure material upon the side of the supporting surface directed toward the patient. This ionization chamber which is always combined with the objects, greatly simplifies the servicing of the X-ray examining apparatus and provides good exposures within the shortest possible time period.

A particularly advantageous embodiment of the present invention is produced when the supporting surface for the exposure material consists of one side of an optically transparent plate. This makes it possible to control with one glance the exact location of the object being examined relatively to the ionization chamber prior to the insertion of the exposure material.

The invention will appear more clearly from the following detailed description when taken in connection with the accompanying drawing showing by way of example only, a preferred embodiment of the inventive idea.

Figure 1:
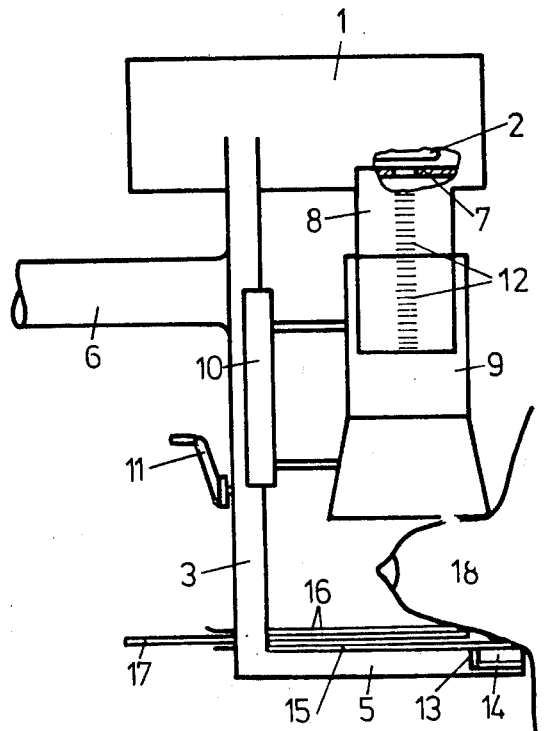
FIG. 1 is a partial side view of an X-ray examining apparatus of the present invention set for vertical ray direction.
Figure 2:
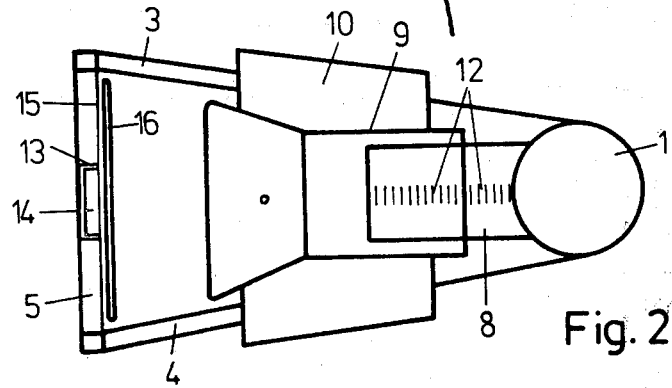
FIG. 2 is a partial illustration of the same apparatus set for horizontal ray direction looking from the side of the patient.

FIGS. 1 and 2 show a casing of an X-ray tube 2 rigidly connected by two carrying beams 3 and 4 with a transparent plate 5 extending perpendicularly to the direction of the rays. A pivot 6 is fixed upon the beams and is used to support the X-ray tube upon a stand (not shown). A diaphragm 7 (FIG. 1) and a tube holder 8 are fixed in front of the ray outlet opening of the X-ray tube 2. A transparent pot-like compression tube 9 faces over the holder and is carried upon a slide 10 movable along the two beams 3 and 4. The slide is mounted so as to be shiftable by a crank 11 in the direction toward the transparent plate 5. Markings 12 are provided upon the tube holder 8, by means of which the position of the compression tube 9 can be read. The transparent plate 5 has on its side directed toward the patient a semi-circular recess 13 in which an ionization chamber 14 is inserted. An optically transparent plastic pocket 16 is located upon the side of the optically transparent plate 5 which serves as a supporting surface 15 for the exposure material. A slide 17 can be pushed into the pocket 16 from the side of the stand. (FIG. 1 shows it as being half pushed in).

Figure 3:
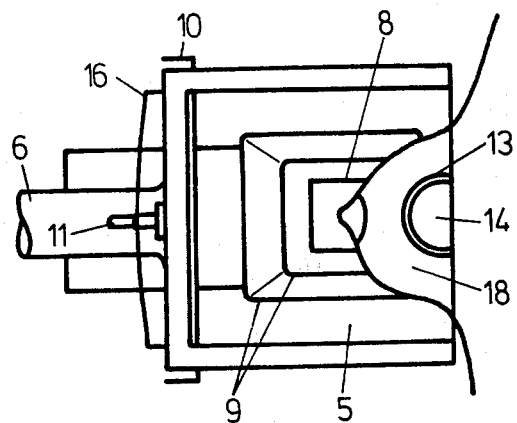
FIG. 3 is a partial illustration of the same apparatus looking in the direction opposed to that of the rays.

FIG. 3 shows the X-ray examining device as having a semi-circular ionization chamber 14 located upon the side of the optically transparent plate 5 which is directed toward the patient. This direction provides at the same time a control of the location of the object 18 being examined relatively to the ionization chamber.

For examining purposes the object 18 being examined is placed between the compression tube 9 and the optically transparent plate 5. By actuating the crank 11, the slide 10 and the compression tube 9 fixed thereon are moved in the direction toward the object being examined and the transparent plate 5. Due to the transparency of the compression tube 9 the object 18 being examined can be observed during the compression procedure as well. The set compression can be reproduced at any time due to the markings 12 provided upon the tube holder 18. The centering of the object being examined relatively to the ionization chamber 14 can be quickly controlled by viewing through the optically transparent plate 5. When the object being examined is properly placed the film slide 17 is pushed into the plastic pocket 16 provided upon the transparent plate and then the exposure is released. After a predetermined film blackening has been completed the X-ray tube is switched off from the ionization chamber by a lighting automat (not shown).

Special tubes having different shapes can be also used to provide removable connections between the tube 9 and the slide 10. It is also possible to arrange the transparent plate 5 in such manner that there will be several constant predetermined distances between the X-ray tube 2 and the supporting surface 15. In that case, however, it is necessary to provide several adapted replaceable screen plate inserts for the X-ray tube.

What is claimed is:

1. Apparatus for X-ray examination of the female breast, having a support rotatable about a horizontal pivot, and comprising in combination, an X-ray tube and first means having a supporting surface for the breast, said X-ray tube and said first means being rigidly fixed on opposed sides of said support, said supporting surface being located perpendicularly in the path of the X-rays being emitted by said X-ray tube, said X-ray tube having a single diaphragm with a constant opening located in front of the X-ray tube and adapted to the size of said supporting surface and it's distance from the X-ray tube, second means responsive to X-rays for providing a visual image of the breast being fixed upon the side of the supporting surface turned towards said X-ray tube, an ionization chamber for switching off said X-ray tube a predetermined dosage having been measured, said ionisation chamber being located at the side of said supporting surface opposite to the X-ray tube and adjacent to the border of the supporting surface directed toward the base of the female breast being examined, a compression device between said X-ray tube and said supporting surface, and means moving said compression device independently of said X-ray tube and the first mentioned means perpendicularly to the plane of said supporting surface, said compression device comprising a solid potlike tube having a flat closed end directed toward said supporting surface and consisting of an optically clear transparent material which does not substantially nearly absorb the X-rays, enabling visual control of the compression of the breast being examined.

2. Apparatus in accordance with claim 1, wherein the first mentioned means comprise an optically clear transparent plate having a side constituting said supporting surface, and a recess for said ionization chamber, enabling visual control of the position of the breast being examined from the side opposite to the X-ray tube.

3. Apparatus in accordance with claim 2, wherein a flat pocket made of an optical clear transparent plastic material is attached upon the side of said transparent plate which is directed toward the X-ray tube enabling said second mentioned means to be pushed in when the breast is compressed without shifting the breast.

* * * * *